United States Patent [19]

Raaf et al.

[11] 4,339,429

[45] Jul. 13, 1982

[54] TOOTHPASTE ACTIVE AGAINST PLAQUE COMPRISING A COPPER COMPOUND AND A PLASTIC POLISHING AGENT

[75] Inventors: Helmut Raaf, Bad Schwalbach; Dieter Becker, Darmstadt-Wixhausen; Franz Frosch, Taunusstein; Helmüt Harth, Mainz; Helmar R. Wägner, Darmstadt, all of Fed. Rep. of Germany

[73] Assignee: Blendax-Werke R. Schneider GmbH & Co., Fed. Rep. of Germany

[21] Appl. No.: 252,406

[22] Filed: Apr. 9, 1981

[30] Foreign Application Priority Data

Apr. 29, 1980 [EP] European Pat. Off. ........ 80102305.2

[51] Int. Cl.³ .......................... A61K 7/16; A61K 7/18; A61K 7/24; A61K 33/34
[52] U.S. Cl. ........................................ 424/49; 424/52; 424/54; 424/55; 424/57; 424/140; 424/143; 424/294; 424/151
[58] Field of Search .................................. 424/49-58, 424/140-143, 294, 151

[56] References Cited

U.S. PATENT DOCUMENTS

| 3,044,939 | 7/1962 | Scanlan et al. | 424/55 |
| 3,070,510 | 12/1962 | Cooley et al. | 424/52 |
| 3,137,632 | 6/1964 | Schiraldi | 424/54 |
| 3,151,027 | 9/1964 | Cooley et al. | 424/52 |
| 3,175,951 | 3/1965 | Tucker et al. | 424/52 |
| 3,325,368 | 6/1967 | Wood | 424/52 |
| 3,538,230 | 11/1970 | Pader et al. | 424/52 |
| 3,662,059 | 5/1972 | Wiesner et al. | 424/52 |
| 3,689,637 | 9/1972 | Pader | 424/52 |
| 3,761,583 | 9/1973 | Gladstone | 424/54 |
| 3,804,946 | 4/1974 | Harrison et al. | 424/52 |
| 3,864,470 | 2/1975 | Watson | 424/49 |
| 3,934,000 | 1/1976 | Barth | 424/49 |
| 4,007,260 | 2/1977 | Kim | 424/52 |
| 4,048,300 | 9/1977 | Tomlinson et al. | 424/52 |
| 4,102,992 | 7/1978 | Davis | 424/49 |
| 4,108,978 | 8/1978 | Mazzanobile et al. | 424/52 |
| 4,144,321 | 3/1979 | Wason | 424/49 |
| 4,146,608 | 3/1979 | Ritchey | 424/54 |
| 4,153,680 | 5/1979 | Seybert | 424/49 |

FOREIGN PATENT DOCUMENTS 367319 5/1974 Sweden .

OTHER PUBLICATIONS

Kempf et al, Chem. Abstracts 32 #4212(7) (1938).
Kempf et al, Chem. Abstracts 31 #7993(8) (1937).
Schmidt Chem. Abstracts 55 #13654(f) (1961).
Manly Drug & Cosmetic Industry 76(3) Mar. 1955: 326, 327, 422, 423, 424, 425.
Wisotzky J. Am. Dent. Assn. 57(6): 796-800, Dec. 1958.
Opperman et al, Chem. Abstracts 94: 114641f Apr. 13, 1981, Scand. J. Dent. RES. (1980) 88(6): 476-480.
Forbes Chem. Abstracts 46: 5662h (1952).

Primary Examiner—Shep K. Rose
Attorney, Agent, or Firm—Linda G. Bierman; Jordan B. Bierman

[57] ABSTRACT

This invention relates to a novel toothpaste and more particularly, to a new toothpaste which includes a finely divided synthetic plastic material as a polishing agent and at least one copper compound. This toothpaste has proven effective against plaque formation on teeth but does not exhibit any of the untoward side effects of the prior art formulations such as discoloring.

11 Claims, No Drawings

TOOTHPASTE ACTIVE AGAINST PLAQUE COMPRISING A COPPER COMPOUND AND A PLASTIC POLISHING AGENT

This invention generally relates to toothpaste and, more particularly, to a new toothpaste having excellent properties for the prevention of the formation of dental plaque on teeth and accordingly makes a significant contribution to the maintenance of healthy teeth and gums.

According to modern dental science, there is no doubt that dental plaque is an important factor in the development of dental caries and also paradontopathies. Therefore, a substantial portion of medico-dental research is directed to discover new substances and means which will prevent plaque formation on teeth. Substantial advances have already been made in this respect. One of the most investigated compounds is 1,6-di-4'-(chlorophenyldiguanido)-hexane, commonly known as "chlorhexidine". This compound not only has an outstanding effect upon bacteria which are responsible for forming dental plaque, it also adheres to the enamel and thus ensures long-lasting action.

In spite of this undisputed success in preventing and combatting parodontopathies, chlorhexidine unfortunately has certain side-effects which although being harmless per se, have hitherto apparently prevented its continuous use in tooth and mouth care preparations.

Extended use of preparations containing chlorhexidine produced discoloration of the teeth and the mucous membranes. This effect is harmless and can be eliminated mechanically, but it is cosmetically undesirable. Its use may also lead to gustatory stimulation or irritation.

More recently, various attempts have been made to discover substances which do not produce these side effects but which still effectively prevent plaque formation on the teeth.

For example, the effectiveness of copper ions has already been discussed in this respect, as shown in AADR Abstracts 1975, No. 117 (Journal of Dental Research 1975, Special Issue A. page 74). Although compounds supplying copper ions have produced satisfactory results in the prevention of plaque formation on teeth when used in solutions in accordance to this reference, surprisingly, it has hitherto been impossible to obtain these results with corresponding toothpastes.

Accordingly, it is an object of the present invention to overcome these disadvantages by providing a novel toothpaste composition containing conventional basic and additive substances, at least one copper compound, and at least one polishing agent which is composed at least for the major part divided synthetic plastic material.

Further objects and advantages of the invention will appear from the following description.

Surprisingly, it has been found, that by using a polishing agent which consists mainly of a finely divided synthetic material a toothpaste containing a copper compound is outstandingly effective against plaque formation on teeth.

The polishing agents consisting of finely divided, powdered synthetic plastic materials are products which are known for this purpose. Usually, they have an average particle diameter of preferably from about 0.5 to about 40 microns and more particularly, from about 2 to about 20 microns. They are present in toothpaste compositions in amounts from about 20% to about 60% by weight.

The preferred polishing agent is polymethyl methacrylate, preferably with an average particle diameter of between about 0.2 and about 5 microns.

It is also possible to use other synthetic plastic materials as a polishing agent in the toothpaste composition. Some of these agents have been disclosed in the prior art and include polyvinyl chloride, polystyrene, polycarbonates, copolymers of methyl methacrylate and other co-monomers, which do not have a negative effect on the hardness and the abrasivity of the methyl methacrylate copolymer; the amount of methyl methacrylate in the copolymer being preferably of at least 80% by weight.

Other suitable polishing agents include polyamides such as powdered nylon, urea-formaldehyde resins, melamineformaldehyde resins, phenol-formaldehyde resins, powdered cured epoxy resins, polyesters and the like. Suitable finely divided synthetic polishing agents are discribed for example in U.S. Pat. Nos. 2,130,034; 3,070,510; 3,151,927; 3,251,800 and in German Accepted Patent Application No. 1,617,306.

In a preferred embodiment, the finely divided synthetic plastic powder is used as the sole polishing agent. However, it is possible to add other polishing agents in minor amounts, that means, in each case, less than 50% of the total amount of polishing agent, provided that the additional polishing agent or agents do not inactivate the copper compounds present.

Such additional polishing agents include, for example, alkali aluminium silicates and in particular, the various silicon dioxides which may be obtained by precipitation. Reference is made to German Published Patent Applications Nos. 2,206,285; 2,446,038, and 2,610,207; British Pat. Nos. 1,433,743 and 1,447,663 and U.S. Pat. No. 3,122,160. These products are commercially available under the names "Neosyl*" and "Sident*".

*Trade Marks

Also suitable for this purpose are the silica xerogels described in U.S. Pat. No. 3,538,230 with specific surfaces of between about 150 and about 800 $m^2/g$ which are commercially available from Grace & Co. under the name Syloid*. Partially dehydrated silica hydrogels as described in German Published Patent Application Nos. 2,704,504 and 2,920,906 may also be used as secondary polishing agent components in the toothpaste composition of the present invention.

*Trade Marks

The amount of the copper compound used in the toothpaste of this invention may be between about 0.001 and about 5% by weight of the total toothpaste, calculated on Cu. The preferred range is from about 0.05 to about 1.5% of copper and the most preferred amount is from about 0.1 to 0.5% of copper.

Suitable copper compounds which supply copper ions are, in principle, all copper compounds being toxicologically harmless, compatible with mucous membranes and, to some extent, water-soluble.

The following inorganic copper salts may be used: Copper chloride, $CuCl_2$, and the dihydrate thereof; copper fluoride, $CuF_2$, and the dihydrate thereof; copper fluorosilicate, $CuSiF_6$, and the hexahydrate thereof; copper sulphate, $CuSO_4$, and the pentahydrate thereof; copper nitrate and the tri- and hexa-hydrates thereof; and also less popular copper salts, such as copper bromide, $CuBr_2$; copper metaborate, $Cu(BO_2)_2$; copper bromate, Cu(BrO$_3$)$_2$.6H$_2$O; copper clorate, Cu(ClO$_3$)$_2$.6H$_2$O; copper iodate, Cu(IO$_3$)$_2$, and copper fluorophosphate, CuPO$_3$F.

Preferred copper salts of organic acids include copper acetate, copper formiate, copper benzoate, copper citrate, copper tartrate, copper lactate, copper malate, copper mandelate, copper sorbate, copper pantothenate, copper gluconate, copper phytate, copper glycerophosphate, copper cinnamate, copper butyrate, copper propionate, copper laurate, copper oxalate, copper glycinate, and copper salicylate.

As stated before, the toothpastes of the present invention contain the usual additives and compounds in addition to the finely divided, powdered synthetic plastic polishing agent and one or more copper compounds.

These include moisturizers such as glycerol and other polyalcohols, for example, propylene glycol, 1,3-butanediol and polyethylene glycols having low molecular weights. Also various sugar alcohols such as sorbitol or mannitol or xylitol may be used.

In addition to these compounds, toothpastes usually contain additional compounds such as thickeners and binding agents. Most suitable in this respect are the various cellulose derivatives (for example, hydroxyalkyl celluloses, and more particulary, hydroxyethyl cellulose), vegetable gums (for example, xanthan gum, carrageen) and inorganic thickeners which are inert to copper ions. The amount of these compounds is generally between about 0.25% and about 3.5% by weight of the toothpaste.

The toothpaste according to the present invention may also contain surfactants which are mainly used to produce a foaming effect which is desired by the customer. Suitable surfactants include water-soluble salts of higher alkyl sulphates or alkyl ether sulphates (e.g. sodium lauryl sulphate), aliphatic acyl amides of saturated monoaminocarboxylic acids (e.g. sodium-N-lauroyl sarcosinate), taurine fatty acid amides (e.g., sodium N-alkyl-N-myristoyl-tauride), salts of sulphonated monoglycerides of higher fatty acids (e.g., sodium monoglyceride sulphonate), fatty acid esters of isethionic acid and salts thereof, non-ionic tensides (e.g., alkylene oxide condensates with fatty alcohols and mono- or polyamines), sugar esters (for example, sucrose monolaurate), sorbitol polyoxyethylene stearate, long-chain amine oxides (e.g., dimethyllauryl amine oxide), ampholytic tensides (e.g., betaine or long-chain alkyl amino carboxylic acids), and cationic tensides (e.g., quaternary ammonium compounds such as cetyltrimethylammonium bromide).

The amount of surfactants in the toothpaste according to the invention is between 0 and about 5% by weight of the total composition.

Toothpastes usually contain flavouring substances, preservatives, etc.. These are known per se and have been described in numerous publications.

In a preferred embodiment of the invention, fluorine compounds are used in amounts providing a fluorine concentration in the paste between 0.01 and 1%, preferably between 0.1 and 0.5% by weight of the toothpaste.

Suitable fluorine compounds are particularly the various salts of monofluorophosphoric acid, especially sodium, potassium, lithium, calcium and aluminum mono- and difluorophosphates, and the various fluorides containing fluorine in ionic form, especially alkali fluorides such as sodium, lithium, potassium and ammonium fluoride, stannous fluoride, manganese fluoride, zirconium fluoride, aluminum fluoride, and mixtures and addition products of these fluorides with each other or with other fluorine compounds, e.g. sodium or potassium manganese fluoride.

Other fluorides that may be used are, e.g., zinc fluoride, germanium fluoride, palladium fluoride, titanium fluoride, alkali fluorozirconates, e.g. sodium or potassium fluorozirconate, stannous fluorozirconate, fluoroborate or fluorosulphate, e.g., sodium or potassium fluorosulphate.

Fluorine and copper ions may also released in a toothpaste according to the invention in the form of one compound, e.g. as copper fluoride, copper monofluorophosphate and copper fluorosilicate.

Organic fluorine compounds may also be used, especially known addition products from long-chain amines or amino acids and hydrogen fluoride, monoethanolamine hydrofluoride or methyltriethylammonium fluoride.

The toothpaste according to the invention may also contain further substances known per se for use in such agents, e.g. enzymes such as proteases and carbohydrases, e.g. amylase, dextranase, levanase or α-1,3-glucan-3-glucanohydrolase; tartar-preventing substances such as phosphonic acids, e.g. hydroxy-ethane-1,1-diphosphonic acid, or bisbiguanidines known for plaque-prevention and their water-soluble salts.

A detailed review of the production of dentifrice preparations and the substances used therefor is given in M.S. BALSAM and E. SAGARIN, "Cosmetics-Science and Technology", 2nd Ed., Vol. 1, pages 423 to 531 (1972).

Examples of toothpastes according to the invention are given hereinafter.

EXAMPLE 1

| | | |
|---|---:|---|
| Xanthan gum | 0.90 | % by weight |
| Glycerol | 15.00 | |
| Sorbitol | 12.00 | |
| CuSO$_4$ . 5 H$_2$O | 0.40 | |
| Sodium monofluorophosphate | 0.76 | |
| Sodium lauryl sulphate | 1.40 | |
| Polymethyl methacrylate powder (average particle diameter ~ 4 μm) | 42.00 | |
| Pyrogenic silica | 2.20 | |
| Flavour mixture | 1.00 | |
| Sodium saccharin | 0.25 | |
| Methyl p-hydroxybenzoate | 0.20 | |
| Deionized water | 23.89 | |

EXAMPLE 2

| | | |
|---|---:|---|
| Carrageen | 0.05 | % by weight |
| Xanthan gum | 0.05 | |
| Glycerol | 7.50 | |
| Sorbitol | 22.00 | |
| Copper formiate . 4 H$_2$O | 0.30 | |
| Copper fluoride (CuF$_2$) | 0.25 | |
| Sodium lauroyl sarcosinate | 2.40 | |
| Cured melamine-formaldehyde condensate (av. particle diam. ≈ 1–10 μm) | 28.50 | |
| Titanium dioxide | 0.50 | |
| Sodium saccharin | 0.10 | |
| Flavour mixture | 1.00 | |
| Methyl p-hydroxybenzoate | 0.10 | |
| n-Propyl p-hydroxybenzoate | 0.05 | |
| Deionized water | 37,20 | |

EXAMPLE 3

| | | |
|---|---|---|
| Hydroxyethyl cellulose | 1.10 | % by weight |
| Glycerol | 10.00 | |
| Sorbitol | 20.00 | |
| Copper fluorosilicate ($CuSiF_6 \cdot 6 H_2O$) | 0.95 | |
| Sodium lauryl sulphate | 1.50 | |
| Finely divided polymethyl methacrylate powder (av. part. diam. $\approx$ 0.5–5 $\mu$m) | 25.00 | |
| Silica aerogel ("Syloid$^R$244", specific surface about 260 m$^2$/g) | 1.80 | |
| Polyvinyl chloride powder (av. part. diam. $\approx$ 1–10 $\mu$m) | 7.30 | |
| Flavour mixture | 1.00 | |
| Sodium saccharin | 0.15 | |
| Methyl p-hydroxybenzoate | 0.20 | |
| Deionized water | 31.00 | |

EXAMPLE 4

| | | |
|---|---|---|
| Methyl cellulose | 1.20 | % by weight |
| 1,3-Butanediol | 6.00 | |
| Glycerol | 13.00 | |
| Sorbitol | 10.00 | |
| Sodium lauryl sulphate (10% suspension in glycerol) | 3.50 | |
| Copper fluoride ($CuF_2 \cdot 2 H_2O$) | 0.30 | |
| Copper pantothenate | 0.80 | |
| Finely divided urea-formaldehyde condensate, cured, av.part.diam. $\sim$ 2–8 $\mu$m) | 37.00 | |
| Flavour mixture | 1.20 | |
| Sodium saccharin | 0.20 | |
| Ethyl p-hydroxybenzoate | 0.13 | |
| Benzoic acid | 0.10 | |
| Tartaric acid | 0.55 | |
| Deionized water | 26.02 | |

EXAMPLE 5

| | | |
|---|---|---|
| Glycerol | 19.00 | % by weight |
| Sorbitol (70%) | 7.00 | |
| Polyethylene glycol 300 | 3.00 | |
| Copper lactate dihydrate | 1.20 | |
| Stannous fluoride ($SnF_2$) | 0.40 | |
| Hydroxyethane-1,1-diphosphonic acid, trisodium salt | 1.25 | |
| Bromochlorophene | 0.05 | |
| Benzoic acid | 0.15 | |
| Dehydracetic acid | 0.10 | |
| n-Propyl p-hydroxybenzoate | 0.05 | |
| Polymethyl methacrylate powder (av.part.diam. $\sim$ 3–8 $\mu$m) | 20.00 | |
| Silica xerogel (of the "Syloid$^R$ 70" type, specific surface about 290 m$^2$/g) | 8.50 | |
| Pyrogenic silica (of the "Aerosil$^R$" type) | 1.20 | |
| Sodium lauryl ether sulphate (25% in ethanol) | 10.00 | |
| Xanthan gum | 0.80 | |
| Deionized water | 27.30 | |

Although preferred embodiments of the invention are described and illustrated it is to be understood that the invention is not restricted to these particular embodiments.

We claim:

1. An aqueous toothpaste composition for reducing or preventing the formation of dental plaque comprising at least one water-soluble copper compound and at least one polishing agent, the major part of said polishing agent being finely divided synthetic plastic material.

2. A method of reducing the formation of dental plaque comprising applying the composition of claim 1 to the teeth.

3. A toothpaste composition as claimed in claim 1, wherein said polishing agent consists, at least partially, of finely divided polymethyl methacrylate.

4. A toothpaste composition as claimed in claim 1, wherein said polishing agent consists, at least partially, of a finely divided aminoplast resin.

5. A toothpaste composition as claimed in claim 1, wherein said synthetic material is selected from the group consisting of polymethyl methacrylate, aminoplast resin, polyvinyl chloride, polystyrene, polycarbonate, powdered nylon, urea-formaldehyde resins, melamine-formaldehyde resins, phenol-formaldehyde resins, and powdered cured epoxy resins.

6. A toothpaste composition as claimed in claim 1, further including one or more additional compatible polishing agents which constitute less than 50% of the total amount of polishing agent.

7. A toothpaste composition as claimed in claim 1, wherein said copper compound is at least one copper salt of an organic acid.

8. A toothpaste composition as claimed in claim 5, wherein said copper compound is at least one water-soluble inorganic copper salt.

9. A toothpaste composition as claimed in claim 7, wherein said copper compound is at least one compound selected from the group consisting of copper citrate, copper tartrate, copper pantothenate, copper lactate, copper malate, copper mandelate, copper sorbate, copper benzoate, copper salicylate, copper gluconate, copper phytate, copper glycerophosphate, copper glycinate and copper cinnamate.

10. A toothpaste composition as claimed in claim 1, wherein said copper compound is present in an amount of between about 0.001% and about 5% by weight, calculated on copper, of the total composition.

11. A toothpaste composition as claimed in claim 10, wherein said copper compound is present in an amount of between about 0.05 and about 0.5% by weight, calculated on copper, of the total composition.

* * * * *